(12) United States Patent
Stasko et al.

(10) Patent No.: US 11,534,382 B2
(45) Date of Patent: Dec. 27, 2022

(54) TOPICAL COMPOSITIONS AND METHODS OF USING THE SAME

(71) Applicant: Novan, Inc., Morrisville, NC (US)

(72) Inventors: Nathan Stasko, Chapel Hill, NC (US); Ryan Doxey, Raleigh, NC (US)

(73) Assignee: Novan, Inc., Durham, NC (US)

( * ) Notice: Subject to any disclaimer, the term of this patent is extended or adjusted under 35 U.S.C. 154(b) by 193 days.

(21) Appl. No.: 16/623,831

(22) PCT Filed: Jun. 19, 2018

(86) PCT No.: PCT/US2018/038185
§ 371 (c)(1),
(2) Date: Dec. 18, 2019

(87) PCT Pub. No.: WO2018/236803
PCT Pub. Date: Dec. 27, 2018

(65) Prior Publication Data
US 2021/0137810 A1    May 13, 2021

Related U.S. Application Data

(60) Provisional application No. 62/521,877, filed on Jun. 19, 2017.

(51) Int. Cl.
| A61K 8/34 | (2006.01) |
| A61K 8/368 | (2006.01) |
| A61K 8/64 | (2006.01) |
| A61K 8/81 | (2006.01) |
| A61K 8/9794 | (2017.01) |
| A61Q 19/00 | (2006.01) |

(52) U.S. Cl.
CPC ............. *A61K 8/64* (2013.01); *A61K 8/345* (2013.01); *A61K 8/368* (2013.01); *A61K 8/8158* (2013.01); *A61K 8/9794* (2017.08); *A61Q 19/00* (2013.01)

(58) Field of Classification Search
IPC ........ A61K 8/64,8/345, 8/368, 8/8158, 8/9794; A61Q 19/00
See application file for complete search history.

(56) References Cited

U.S. PATENT DOCUMENTS

| 8,241,650 B2 | 8/2012 | Peters |
| 8,282,967 B2 | 10/2012 | Schoenfisch et al. |
| 8,399,005 B2 | 3/2013 | Schoenfisch et al. |
| 8,591,876 B2 | 11/2013 | Bauman et al. |
| 8,937,143 B2 | 1/2015 | Bao et al. |
| 8,956,658 B2 | 2/2015 | Schoenfisch et al. |
| 8,962,029 B2 | 2/2015 | Schoenfisch et al. |
| 8,981,139 B2 | 3/2015 | Schoenfisch et al. |
| 9,187,501 B2 | 11/2015 | Schoenfisch et al. |
| 9,238,038 B2 | 1/2016 | Schoenfisch et al. |
| 9,289,442 B2 | 3/2016 | Doxey et al. |
| 9,381,381 B2 | 7/2016 | Benjamin |
| 9,427,605 B2 | 8/2016 | Peters |
| 9,669,041 B2 | 6/2017 | Stasko et al. |
| 9,757,397 B2 | 9/2017 | Kougoulos et al. |
| 9,855,211 B2 | 1/2018 | Doxey et al. |
| 10,206,947 B2 | 2/2019 | Doxey et al. |
| 10,258,564 B2 | 4/2019 | Doxey et al. |
| 10,322,081 B2 | 6/2019 | McHale et al. |
| 2005/0009717 A1 | 1/2005 | Lukenbach et al. |
| 2006/0110415 A1* | 5/2006 | Gupta .................. A61K 8/0212 424/59 |
| 2006/0134156 A1 | 6/2006 | Marion |
| 2006/0173072 A1 | 8/2006 | Yamaguchi et al. |
| 2006/0269620 A1 | 11/2006 | Morris et al. |
| 2008/0107679 A1* | 5/2008 | Dilallo .................... A61K 8/64 424/195.17 |
| 2009/0214618 A1 | 8/2009 | Schoenfisch et al. |
| 2010/0098733 A1 | 4/2010 | Stasko et al. |
| 2010/0239512 A1 | 9/2010 | Morris |
| 2010/0331968 A1 | 12/2010 | Morris et al. |
| 2011/0052650 A1 | 3/2011 | Morris et al. |
| 2011/0086234 A1 | 4/2011 | Stasko et al. |
| 2012/0134951 A1 | 5/2012 | Stasko et al. |

(Continued)

FOREIGN PATENT DOCUMENTS

| WO | 2010044875 | 4/2010 |
| WO | 2011022652 | 2/2011 |

(Continued)

OTHER PUBLICATIONS

Schaefer, Katie "Menthol Derivative Cooling Agent" Cosmetics & Toiletries (https://www.cosmeticsandtoiletries.com/formulating/function/feelenhancer/134359173.html) (Nov. 28, 2011).
EWG's Skin Deep Cosmetics Database "Dimethicone/Vinyl Dimethlcone Crosspolymer" https://www.ewg.org/skirideep/ingredient/702043/DIMETHICONE/_VINYL_DIMETHICONE_CR (2 pages) (Published: May 31, 2017; Retrieved Aug. 17, 2018).
Herro et al. "Mentha piperita (peppermint)" Dermatitis, 21(6):327-329 (2010) (Abstract only).
International Preliminary Report on Patentability corresponding to International Patent Application No. PCT/US2018/038185 (6 pages) (dated Jan. 2, 2020).
MISSHA "Super Aqua ice Tear Sleeping Mask" https://shop.missha-deutschland.de/MISSHA-Super-Aqua-Ice-Tear-Sleeping-Mark/en (3 pages) (Published: Feb. 11, 2017; Retrieved: Aug. 17, 2018).

(Continued)

*Primary Examiner* — Julie Ha
*Assistant Examiner* — Kristina M Hellman
(74) *Attorney, Agent, or Firm* — Myers Bigel, P.A.

(57) ABSTRACT

The present invention relates generally to compositions and methods of using the same such as, for example, methods of treating the skin of a subject using a composition as described herein. The composition may comprise a diluent, a solvent, a penetration enhancing agent, a skin brightening agent, a skin renewing agent, a thickening agent, an anti-irritant, a chelating agent, an active pharmaceutical ingredient (API), optionally a pH adjustment agent, and optionally a preservative. The composition may further comprise L-arginine and/or L-citrulline and/or esters and/or derivatives thereof.

19 Claims, No Drawings

Specification includes a Sequence Listing.

(56) References Cited

U.S. PATENT DOCUMENTS

| | | |
|---|---|---|
| 2012/0136323 A1 | 5/2012 | Stasko et al. |
| 2013/0310533 A1 | 11/2013 | Bao et al. |
| 2013/0344334 A1 | 12/2013 | Schoenfisch et al. |
| 2014/0112959 A1 | 4/2014 | Johnson et al. |
| 2014/0134321 A1 | 5/2014 | Stasko et al. |
| 2015/0024052 A1 | 1/2015 | Doxey |
| 2015/0064224 A1 | 3/2015 | Tong et al. |
| 2015/0111973 A1 | 4/2015 | Bauman et al. |
| 2016/0106657 A9 | 4/2016 | Peters |
| 2016/0199295 A1 | 7/2016 | Doxey et al. |
| 2017/0196905 A1 | 7/2017 | Doxey et al. |
| 2018/0055065 A1 | 3/2018 | Schoeppe et al. |
| 2018/0200541 A1 | 7/2018 | Doxey et al. |
| 2018/0319822 A1 | 11/2018 | Schoenfisch et al. |
| 2018/0353392 A1 | 12/2018 | Schmaus et al. |

FOREIGN PATENT DOCUMENTS

| | | |
|---|---|---|
| WO | 2011022680 | 2/2011 |
| WO | 2011047013 | 4/2011 |
| WO | 2012082976 | 6/2012 |
| WO | 2012100174 | 7/2012 |
| WO | 2012118829 | 7/2012 |
| WO | 2012118819 | 9/2012 |
| WO | 2013006608 | 1/2013 |
| WO | 2013006613 | 1/2013 |
| WO | 2013029009 | 2/2013 |
| WO | 2013063354 | 5/2013 |
| WO | 2013138073 | 9/2013 |
| WO | 2013138075 | 9/2013 |
| WO | 2014028847 | 2/2014 |
| WO | 2014134502 | 9/2014 |
| WO | 2015021382 | 2/2015 |
| WO | 2016007834 | 1/2016 |
| WO | 2016010988 | 1/2016 |
| WO | 2016022170 | 2/2016 |
| WO | 2016160089 | 10/2016 |
| WO | 2017011031 | 1/2017 |
| WO | 2017019614 | 2/2017 |
| WO | 2017151905 | 9/2017 |
| WO | 2017180822 | 10/2017 |
| WO | 2018189687 | 10/2018 |
| WO | 2018236806 | 12/2018 |
| WO | 2019169221 | 9/2019 |
| WO | 2019232166 | 12/2019 |

OTHER PUBLICATIONS

"Polysorbate 20" https://en.wikipedia.org/w/index.php?title=Polysorbate_20&oldid=758125799 (3 pages) (Published: Jan. 3, 2017; Retrieved: Aug. 17, 2018).

Thickening agent https://en.wikipedia.org/w/index.php?title=Tickening_agent&oldid=783372206 (5 pages) (Published: Jun. 1, 2017; Retrieved: Aug. 17, 2018).

Bellatorra "Tripeptide-1" http://bellatorra.com/tripeptide-1/ (1 page) (Jan. 16, 2017).

International Search Report and the Written Opinion of the International Searching Authority corresponding to International Patent Application No. PCT/US2018/038185 (9 pages) (dated Sep. 24, 2018).

Leaderma "Collagen Booster Serum" www.leaderma.com/cbs.html (1 page) (Published: Oct. 18, 2016; Retrieved: Aug. 17, 2018).

Leschke, M. "Ethylhexylglycerin for a Improved Skin Feel" SOFW Journal, 136:9-14 (2010).

Lotioncrafter "Hydrolyzed Wheat Protein" https://www.lotioncrafter.com/hydrolyzed-wheat-protein.html (2 pages) (Published: Jun. 6, 2017; Retrieved: Aug. 17, 2018).

"This Is the Best Essential Oil for Skin Lightening" https://www.themiracleofessentialoils.com/the-best-essential-oil-for-skin-lightening/ (7 pages) (Published: Jun. 16, 2017; Retrieved: Aug. 17, 2017).

Truth in Aging "Acrylates C10-30 Alkyl Acrylate Cross Polymer" http://www.truthinaging.com:80/ingredients/acrylates-c10-30-alkyl-acrylate-cross-polymer (2 pages) (Published: Aug. 9, 2014; Retrieved: Aug. 17, 2018).

Truth in Aging "Citrulline" http://www.truthinaging.com:80/ingredients/citrulline (2 pages) (Published: Oct. 23, 2013; Retrieved: Aug. 17, 2018).

Truth in Aging "Disodium EDTA" http://www.truthinaging.com/ingredients/disodium-edta (2 pages) (Published: Nov. 14, 2016; Retrieved: Aug. 17, 2018).

Truth in Aging "Tripeptide-10 Citrulline" http://www.truthinaging.com/review/new-watch-out-for-tripeptide-10-citrulline (2 pages) (Published: Aug. 28, 2014; Retrieved: Aug. 17, 2018).

\* cited by examiner

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Pro Lys Glu Lys
1
```

TOPICAL COMPOSITIONS AND METHODS OF USING THE SAME

RELATED APPLICATION INFORMATION

This application is a 35 U.S.C. § 371 national phase application of International Application No. PCT/US2018/038185, filed Jun. 19, 2018, which claims the benefit of and priority to U.S. Provisional Patent Application Ser. No. 62/521,877, filed Jun. 19, 2017, the disclosure of each of which is incorporated herein by reference in their entirety.

STATEMENT REGARDING ELECTRONIC FILING OF A SEQUENCE LISTING

A Sequence Listing in ASCII text format, submitted under 37 C.F.R. § 1.821, entitled 9729.83_ST25, 520 bytes in size, generated on Aug. 11, 2022, and filed via EFS-Web, is provided in lieu of a paper copy. This Sequence Listing is hereby incorporated herein by reference into the specification for its disclosures.

FIELD

The present invention relates generally to compositions and methods of using the same.

BACKGROUND

Skin may be cleaned and/or treated with various compositions. The present invention addresses previous shortcomings in the art by providing topical compositions and methods of using the topical compositions.

SUMMARY

A first aspect of the present invention is directed to a composition, the composition comprising: a diluent, a solvent, a penetration enhancing agent, a skin brightening agent, a skin renewing agent, a thickening agent, an anti-irritant, a chelating agent, an active pharmaceutical ingredient (API), optionally a pH adjustment agent, and optionally a preservative. In some embodiments, the composition comprises L-arginine and/or L-citrulline and/or esters and/or derivatives thereof. The composition may be cosmetically elegant. The composition may be a pharmaceutical composition.

A further aspect of the present invention is directed to a kit comprising a composition of the present invention.

Another aspect of the present invention is directed to a method of treating a subject, the method comprising applying a composition of the present invention to the skin of the subject. A therapeutically effective amount of the composition may be applied.

Another aspect of the present invention is directed to a method of treating acne vulgaris comprising topically applying a composition of the present invention to the skin of a subject. A therapeutically effective amount of the composition may be applied.

A further aspect of the present invention is directed to a method of reducing inflammatory and/or noninflammatory lesions in a subject comprising topically applying a composition of the present invention to the skin of the subject. A therapeutically effective amount of the composition may be applied. The method may reduce inflammatory and/or noninflammatory lesions by about 10% or greater over a defined period of time compared to a subject who did not apply a composition of the present invention over the same time period. The subject may see a reduction in inflammatory and/or noninflammatory lesions within 12 weeks or less, in some embodiments, within 8 weeks or less, and in further embodiments, within 4 weeks or less.

Another aspect of the present invention is directed to a method of reducing *P. acnes* counts in a subject comprising topically applying a composition of the present invention to the skin of the subject. A therapeutically effective amount of the composition may be applied. The method may reduce *P. acnes* counts by about 10% or greater over a defined period of time compared to a subject who did not apply a composition of the present invention over the same time period. The subject may see a reduction in *P. acnes* counts within 12 weeks or less, in some embodiments, within 8 weeks or less, and in further embodiments, within 4 weeks or less.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as an amount or concentration and the like, is meant to refer to variations of up to ±20% of the specified value, such as, but not limited to, ±10%, ±5%, ±1%, ±0.5%, or even ±0.1% of the specified value, as well as the specified value. For example, "about X" where X is the measurable value, is meant to include X as well as variations of ±20%, ±10%, ±5%, ±1%, ±0.5%, or even ±0.1% of X. A range provided herein for a measureable value may include any other range and/or individual value therein.

According to some embodiments of the present invention, provided herein are topical compositions. A composition of the present invention may comprise an active pharmaceutical ingredient (API), a diluent, a solvent, a penetration enhancing agent, a skin brightening agent, a skin renewing agent, a thickening agent, an anti-irritant, a pH adjustment agent, a chelating agent, a preservative, L-arginine, L-citrulline, and/or an ester and/or derivative of L-arginine and/or L-citrulline.

One or more (e.g., 1, 2, 3, 4, 5, or more) diluent(s) may be present in the composition. Example diluents include, but are not limited to, water. In some embodiments, a diluent is present in an amount of about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, or 95% by weight of the composition. In some embodiments, the total amount of the one or more diluents in the composition is about 40%, 50%, 60%, or 70% to about 75%, 80%, 85%, 90%, or 95% by weight of the composition. In some embodiments, the one or more diluents make up the balance of the composition to total 100% by weight of the composition.

One or more (e.g., 1, 2, 3, 4, 5, or more) solvent(s) may be present in the composition. Example solvents include, but are not limited to, alcohols, such as, e.g., tert-butyl alcohol (e.g., Specially Denatured Alcohol (SDA) 40B, 190 proof, commercially available from Sigma-Aldrich). In some embodiments, a solvent may be present in the composition in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the composition. In some embodiments, a solvent may be present in the composition in an amount of about 1%, 2%, 3%, 4%, or 5% to about 6%, 7%, 8%, 9%, 10%, 11%1, 2%1, 3%1, 4%1, 5%1, 6%1, 7%, 18%, 19%, or 20% by weight of the composition. In some embodiments, the total amount of the one or more solvent(s) in the composition is about 1%, 2%, 3%, 4%, 5%, 6%, 7%, 8%, 9%, 10%, 11%, 12%, 13%, 14%, 15%, 16%, 17%, 18%, 19%, or 20% by weight of the composition. In some embodiments, the total amount of the one or more solvent(s) in the composition is about 1%, 2%, 3%, 4%, or 5% to about 6%, 7%, 8%, 9%, 10%1, 11%, 12%, 13%, 14%, 15%, 16%, 17%, 18%, 19%, or 20% by weight of the composition.

One or more (e.g., 1, 2, 3, 4, 5, or more) penetration enhancing agent(s) may be present in the composition. Example penetration enhancing agents include, but are not limited to, glycol ethers, such as, e.g., ethoxydiglycol (e.g., those commercially available from Gattefosse under the tradename Transcutol®, e.g., Transcutol® P). In some embodiments, a penetration enhancing agent may be present in the composition in an amount of about 1%, 2%, 3%, 4%, 5%, 6%, 7%, 8%, 9%, 10%, 11%, 12%, 13%, 14%, or 15% by weight of the composition. In some embodiments, a penetration enhancing agent may be present in the composition in an amount of about 1%, 2%, 3%, or 4% to about 5%, 6%, 7%, 8%, 9%, 10%, 11%, 12%, 13%, 14%, or 15% by weight of the composition. In some embodiments, the total amount of the one or more penetration enhancing agent(s) in the composition is about 1%, 2%, 3%, 4%, 5%, 6%, 7%, 8%, 9%, 10%, 11%, 12%, 13%, 14%, or 15% by weight of the composition. In some embodiments, the total amount of the one or more penetration enhancing agent(s) in the composition is about 1%, 2%, 3%, or 4% to about 5%, 6%, 7%, 8%, 9%, 10%, 11%, 12%, 13%, 14%, or 15% by weight of the composition.

One or more (e.g., 1, 2, 3, 4, 5, or more) skin brightening agent(s) may be present in the composition. Example skin brightening agents include, but are not limited to, peptide compositions, such as, e.g., those commercially available from Evonik Nutrition & Care GmbH under the tradename TEGO® Pep 4-Even that contains Tetrapeptide-30, which is the amino acid sequence Proline-Lysine-Glutamic Acid-Lysine (PKEK, SEQ ID NO:1), in glycerin and water. The skin brightening agent may reduce hyperchromatic spots, brighten skin to which it is applied, reduce acne lesions, and/or alleviate melasma. In some embodiments, a skin brightening agent may be present in the composition in an amount of about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by weight of the composition. In some embodiments, a skin brightening agent may be present in the composition in an amount of about 0.1%, 0.5%, 1%, 1.5%, 2%, or 2.5% to about 3%, 3.5%, 4%, 4.5%, 5%, 5.5%, 6%, 6.5%, 7%, 7.5%, 8%, 8.5%, 9%, 9.5%, or 10% by weight of the composition. In some embodiments, the total amount of the one or more skin brightening agent(s) in the composition is about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by weight of the composition. In some embodiments, the total amount of the one or more skin brightening agent(s) in the composition is about 0.1%, 0.5%, 1%, 1.5%, 2%, or 2.5% to about 3%, 3.5%, 4%, 4.5%, 5%, 5.5%, 6%, 6.5%, 7%, 7.5%, 8%, 8.5%, 9%, 9.5%, or 10% by weight of the composition.

One or more (e.g., 1, 2, 3, 4, 5, or more) skin renewal agent(s) may be present in the composition. Example skin renewal agents include, but are not limited to, peptide compositions, such as, e.g., those commercially available from Lucas Meyer Cosmetics under the tradename Kollaren™ PS 100 that contains Tripeptide-1 in glycerin and dextran. The skin renewal agent may increase skin firmness and/or stimulate the production of the extra cellular matrix (ECM) components such as collagen I, collagen III, fibronectin, elastin, and/or laminin. In some embodiments, a skin renewal agent may be present in the composition in an amount of about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by weight of the composition. In some embodiments, a skin renewal agent may be present in the composition in an amount of about 0.1%, 0.5%, 1%, 1.5%, or 2% to about 2.5%, 3%, 3.5%, 4%, 4.5%, 5%, 5.5%, 6%, 6.5%, 7%, 7.5%, 8%, 8.5%, 9%, 9.5%, or 10% by weight of the composition. In some embodiments, the total amount of the one or more skin renewal agent(s) in the composition is about 0.1%, 0.5%, 1%, 1.5%, 2%, 2.5%, 3%, 3.5%, 4%, 4.5%, 5%5.5%, 6%, 6.5%, 7%, 7.5%, 8%, 8.5%, 9%, 9.5%, or 10% by weight of the composition. In some embodiments, the total amount of the one or more skin renewal agent(s) in the composition is about 0.1%, 0.5%, 1%, 1.5%, or 2% to about 2.5%, 3%, 3.5%, 4%, 4.5%, 5%, 5.5%, 6%, 6.5%, 7%, 7.5%, 8%, 8.5%, 9%, 9.5%, or 10% by weight of the composition.

One or more (e.g., 1, 2, 3, 4, 5, or more) thickening agent(s) may be present in the composition. Example thickening agents include, but are not limited to, polyacrylate polymers, such as, e.g., those commercially available from Seppic under the tradename Sepimax Zen™. In some embodiments, a thickening agent may be present in the composition in an amount of about 0.1%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% by weight of the composition. In some embodiments, a thickening agent may be present in the composition in an amount of about 0.1%, 0.5%, 1%, or 1.5% to about 2%, 2.5%, 3%, 3.5%, 4%, 4.5%, 5%, 5.5%, 6%, 6.5%, 7%, 7.5%, 8%, 8.5%, 9%, 9.5%, or 10% by weight of the composition. In some embodiments, the total amount of the one or more thickening agent(s) in the composition is about 0.1%, 0.5%, 1%, 1.5%, 2%, 2.5%, 3%, 3.5% 4%, 4.5% 5%, 5.5% 6%, 6.5%, 7%, 7.5% 8%, 8.5%, 9%, 9.5%, or 10% by weight of the composition. In some embodiments, the total amount of the one or more thickening agent(s) in the composition is about 0.1%, 0.5%, 1%, or 1.5% to about 2%, 2.5%, 3%, 3.5%, 4%, 4.5% 5%, 5.5% 6%, 6.5%, 7%, 7.5%, 8%, 8.5%, 9%, 9.5% or 10% by weight of the composition.

One or more (e.g., 1, 2, 3, 4, 5, or more) anti-irritant(s) may be present in the composition. Example anti-irritants include, but are not limited to, synthetic avenanthramides, such as, e.g., those commercially available from Symrise under the tradename SymCalmin® that contain butylene glycol (and) pentylene glycol (and) hydroxyphenyl propamidobenzoic acid; SymRelief® 100 that contains bisabolol (and) Zingiber officinale (ginger) root extract commercially available from Symrise; and any combination thereof. In some embodiments, an anti-irritant may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the composition. In some embodiments, an anti-irritant may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, or 0.5% to about 0.6%, 0.7%, 0.8%, 0.9%, 1%, 1.5%, 2%, 2.5%, 3%, 3.5%, 4%, 4.5%, or 5% by weight of the composition. In some embodiments, the total amount of the one or more anti-irritant(s) in the composition is about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the composition. In some embodiments, the total amount of the one or more anti-irritant(s) in the composition is about 0.01%, 0.02%, 0.03%, 0.04%, 0.05%, 0.06%, 0.07%, 0.08%, 0.09%, 0.1%, 0.2%, 0.3%, 0.4%, or 0.5% to about 0.6%, 0.7%, 0.8%, 0.9%, 1%, 1.5%, 2%, 2.5%, 3%, 3.5%, 4%, 4.5%, or 5% by weight of the composition.

One or more (e.g., 1, 2, 3, 4, 5, or more) pH adjustment agent(s) may be present in the composition. Example pH adjustment agents include, but are not limited to, bases such as, e.g., sodium hydroxide, potassium hydroxide, and mixtures thereof; acids such as, e.g. hydrochloric acid, citric acid, lactic acid, glycolic acid, acetic acid, and mixtures thereof; sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof. In some embodiments, a pH adjustment agent may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, a pH adjustment agent may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, or 0.5% to about 0.6%, 0.7%, 0.8%, 0.9%, 1%, 1.5%, 2%, 2.5%, or 3% by weight of the composition. In some embodiments, the total amount of the one or more pH adjustment agent(s) in the composition is about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, the total amount of the one or more pH adjustment agent(s) in the composition is about 0.01%, 0.02%, 0.03%, 0.04%, 0.05%, 0.06%, 0.07%, 0.08%, 0.09%, 0.1%, 0.2%, 0.3%, 0.4%, or 0.5% to about 0.6%, 0.7%, 0.8%, 0.9%, 1%, 1.5%, 2%, 2.5%, or 3% by weight of the composition.

One or more (e.g., 1, 2, 3, 4, 5, or more) preservative(s) may be present in the composition. Example preservatives include, but are not limited to, sorbic acid, benzoic acid, methyl-paraben, propyl-paraben, methylchloroisothiazolinone, metholisothiazolinone, diazolidinyl urea, chlorobutanol, triclosan, benzethonium chloride, p-hydroxybenzoate, chlorhexidine, digluconate, hexadecyltrimethyl ammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, phenoxyethanol (and) ethylhexylglycerin (e.g., EUXYL® PE 9010 commercially available from Schilke Inc.), and any combination thereof. In some embodiments, a preservative may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, a preservative may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, or 0.5% to about 0.6%, 0.7%, 0.8%, 0.9%, 1%, 1.5%, 2%, 2.5%, or 3% by weight of the composition. In some embodiments, the total amount of the one or more preservative(s) in the composition is about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, the total amount of the one or more preservative(s) in the composition is about 0.01%, 0.02%, 0.03%, 0.04%, 0.05%, 0.06%, 0.07%, 0.08%, 0.09%, 0.1%, 0.2%, 0.3%, 0.4%, or 0.5% to about 0.6%, 0.7%, 0.8%, 0.9%, 1%, 1.5%, 2%, 2.5%, or 3% by weight of the composition.

One or more (e.g., 1, 2, 3, 4, 5, or more) chelating agent(s) may be present in the composition. Example chelating agents include, but are not limited to, tetrasodium salt of ethylenediaminetetraacetate (EDTA) (e.g., VERSENE™ 100 XL commercially available from The Dow Chemical Company); disodium salt of EDTA (e.g., VERSENE™ NA commercially available from The Dow Chemical Company); and combinations thereof. In some embodiments, a chelating agent may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, a chelating agent may be present in the composition in an amount of about 0.01%, 0.02%, 0.03%, 0.04%, 0.05%, 0.06%, 0.07%, 0.08%, or 0.09% to about 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, the total amount of the one or more chelating agent(s) in the composition is about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, or 3% by weight of the composition. In some embodiments, the total amount of the one or more chelating agent(s) in the composition is about 0.01%, 0.02%, 0.03%, 0.04%, 0.05%, 0.06%, 0.07%, 0.08%, or 0.09% to about 0.1%, 0.2%, 0.3%, 0.4%, 0.5%, 0.6%, 0.7%, 0.8%, 0.9%, 1%, 1.5%, 2%, 2.5%, or 3% by weight of the composition.

A composition of the present invention may comprise an active pharmaceutical ingredient (API). Any suitable API or combinations of APIs may be included in a composition of the present invention. Example APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofilm agents, and any combination thereof. Example APIs include, but are not limited to, those described in International Application Publication No. WO 2013/006608, which is incorporated herein by reference in its entirety. In some embodiments, a composition of the present invention may not comprise an API.

In some embodiments, the composition comprises an API and the API is an anti-acne agent. One or more (e.g., 1, 2, 3, 4, 5, or more) anti-acne agents may be present in the composition. In some embodiments, the API is salicylic acid. Salicylic acid may be about present in the composition in an amount of about 0.1%, 0.5%, 1%, 2%, 3%, 4%, 5%, 6%, 7%, 8%, 9%, or 10% by weight of the composition. In some embodiments, salicylic acid is present in the composition in an amount of about 0.1%, 0.5%, 1%, or 1.5% to about 2%, 2.5%, 3%, 3.5%, 4%, 4.5%, or 5% by weight of the composition.

In some embodiments, the API may comprise an NO-releasing API, such as, but not limited to a diazeniumdiolate modified macromolecule. "Nitric oxide releasing active pharmaceutical ingredient" and "NO releasing API," as used herein, refer to a compound or other composition that provides nitric oxide to the skin of a subject, but is not only gaseous nitric oxide. In some embodiments, the NO releasing API includes a nitric oxide-releasing compound, hereinafter referred to as a "NO-releasing compound." An NO-releasing compound includes at least one NO donor, which is a functional group that may release nitric oxide under certain conditions.

Any suitable NO-releasing compound may be used. In some embodiments, the NO-releasing compound includes a small molecule compound that includes an NO donor group. "Small molecule compound" as used herein is defined as a compound having a molecular weight of less than 500 daltons, and includes organic and/or inorganic small molecule compounds. In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 µm and may comprise the aggregation of two or more macromolecules, whereby the macromolecular structure is further modified with an NO donor group.

In some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in a second composition as described herein. Additionally, the NO donor may be incorporated into or onto the small molecule or macromolecule through covalent and/or non-covalent interactions.

An NO-releasing macromolecule may be in the form of an NO-releasing particle, such as those described in U.S. Pat. No. 8,282,967, 8,962,029 or 8,956,658, the disclosures of which are incorporated by reference herein in their entirety. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in International Application No. PCT/US2012/052350 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the present invention, a nitric oxide-releasing active pharmaceutical ingredient may include NO-loaded precipitated silica. The NO-loaded precipitated silica may be formed from nitric oxide donor modified silane monomers into a co-condensed siloxane network. In one embodiment of the present invention, the nitric oxide donor may be an N-diazeniumdiolate. In some embodiments of the present invention, the nitric oxide-releasing active pharmaceutical ingredient may comprise, consist essentially of, or consist of a co-condensed siloxane network comprising a diazeniumdiolate (e.g., a N-diazeniumdiolate).

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors. In some embodiments of the present invention, the nitric oxide-releasing active pharmaceutical ingredient may comprise, consist essentially of, or consist of a co-condensed silica network synthesized from the condensation of a silane mixture comprising an alkoxysilane and at least one aminoalkoxysilane having an amine substituted by a diazeniumdiolate (e.g., a N-diazeniumdiolate).

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''—(NH—R')_n—Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl] trimethoxysilane (MAP3); N-butylamino-propyltrimethoxysilane(n-BAP3); t-butylamino-propyltrimethoxysilane(t-BAP3); N-ethylaminoisobutyltrimethoxysilane(EAiB3); N-phenylamino-propyltrimethoxysilane (PAP3); and N-cyclohexylaminopropyltrimethoxysilane (cHAP3).

In some embodiments, the aminoalkoxysilane has the formula: $NH[R'—Si(OR)_3]_2$, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: $R''—N(NONO—X^+)—R'—Si(OR)_3$, wherein R is alkyl, R' is alkylene or aralkylene, R" is alkyl or alkylamine, and X+ is a cation selected from the group consisting of $Na^+$, $K^+$ and $Li^+$.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In some embodiments, the amino group of aminoalkoxysilane is substituted with a diazeniumdiolate, and the aminoalkoxysilane having a formula of $R''—N(NONO—X^+)—R'—Si(OR)^3$, wherein: R is alkyl, R' is alkylene or aralkylene, R" is alkyl or alkylamine, and $X^+$ is a cation selected from the group consisting of $Na^+$ and $K^+$.

In some embodiments, the NO-releasing API may comprise a co-condensed silica network comprising diazeniumdiolated aminoethylaminopropyl trimethoxy silane (AEAP3) and tetra methyl orthosilicate (TMOS) and/or a co-condensed silica network comprising diazeniumdiolated aminoethylaminopropyl trimethoxy silane (AEAP3) and tetraethyl orthosilicate (TEOS). In some embodiments, the NO-releasing API may comprise a co-condensed silica network comprising diazeniumdiolated methylaminopropyl trimethoxysilane (MAP3) and tetra methyl orthosilicate (TMOS) and/or a co-condensed silica network comprising diazeniumdiolated methylaminopropyl trimethoxysilane (MAP3) and tetraethyl orthosilicate (TEOS). In some embodiments, the NO-releasing API may comprise a co-condensed silica network comprising diazeniumdiolated methylaminopropyl trimethoxysilane (MAP3), ethylaminoisobutylsiloxane (EAIB3), and tetraethyl orthosilicate (TEOS). In some embodiments, the NO-releasing API may be ethylaminoisobutylsiloxane/methylaminopropylsiloxane-co-polysiloxane (EAIB3:MAP3-NONOate/TEOS). In some embodiments, the NO-releasing API may comprise an amorphous polymer.

In some embodiments of the invention, the particle size of a NO-releasing API may be in a range of about 20 nm to about 20 μm or any range therein, such as, but not limited to, about 100 nm to about 20 μm or about 1 μm to about 20 μm. The particle size may be tailored to minimize or prevent toxicity and/or penetration through the epidermis (or compromised dermis) and into the blood vessels. In particular embodiments, the particle size is distributed around a mean particle size of less than 20 μm, or any range therein, and the size may allow the particle to enter a follicle. In some embodiments, a NO-releasing API may have a particle size that is distributed around a mean particle size of about 20, 19, 18, 17, 16, 15, 14, 13, 12, 11, 10, 9, 8, 7, 6, 5, 4, 3, 2, or 1 μm. In some embodiments, a NO-releasing API may have a particle size that is distributed around a mean particle size of less than 10 μm, or any range therein, such as, but not limited to about 2 μm to about 10 μm or about 4 μm to about 8 μm. In some embodiments, the particle size may be distributed around a mean particle size of greater than 20 μm, or any range therein, and the size may prevent the particle from entering the follicle. In some embodiments, a mixture of particles with mean particle sizes distributed around two or more mean particle sizes may be provided. A NO-releasing API may be micronized (e.g., ball and/or jet milled). Methods for providing a desired particle size and/or micronization include, but are not limited to, those described in U.S. Patent Application Publication No. 2013/0310533, which is incorporated herein by reference in its entirety.

A nitric oxide-releasing active pharmaceutical ingredient may be present in a composition of the present invention in an amount of about 0.5% to about 10% by weight of the composition, such as, but not limited to, about 1% to about 8% or about 2% to about 6% by weight of the composition. In some embodiments, a nitric oxide-releasing active pharmaceutical ingredient may be present in a composition of the present invention in an amount of about 0.5%, 1%, 2%, 3%, 4%, 5%, 6%, 7%, 8%, 9%, or 10% by weight of the composition. In some embodiments, a nitric oxide-releasing active pharmaceutical ingredient is present in a composition of the present invention in an amount of about 0.5%, 10%, or 2% to about 3%, 4%, 5%, 6%, 7%, 8%, 9%, or 10% by weight of the composition. A composition of the present invention may comprise a nitric oxide-releasing active pharmaceutical composition and may store and/or release nitric oxide in an amount of about 0.05% to about 3% by weight of composition, such as, but not limited to, about 0.15% to about 2%, about 0.15% to about 1%, about 0.3% to about 1.2% by weight of the composition. In certain embodiments, a composition of the present invention may comprise a nitric oxide-releasing active pharmaceutical and may store and/or release nitric oxide in an amount of about 0.15%, 0.3%, 0.6%, 0.9%, 1%, 1.2%, 1.5%, 1.75%, 2%, 2.25%, 2.5%, 2.75%, or 3% by weight of the composition.

L-arginine and/or L-citrulline and/or esters and/or derivatives thereof may be present in a composition of the present invention. In some embodiments, L-arginine and/or L-citrulline and/or esters and/or derivatives thereof may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the composition. In some embodiments, L-arginine and/or L-citrulline and/or esters and/or derivatives thereof may be present in the composition in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% to about 1.5%, 2%, 2.5%, 3%, 3.5%, 4%, 4.5%, or 5% by weight of the composition.

In some embodiments, L-arginine and L-citrulline and/or esters and/or derivatives thereof may be present in a composition of the present invention in a ratio of about 3:1 to about 1:3 (i.e., L-arginine and/or esters and/or derivatives thereof to L-citrulline and/or esters and/or derivatives thereof), such as, e.g., about 3:1, 2:1, 1:1, 1:2, or 1:3. In some embodiments, L-arginine and L-citrulline and/or esters and/or derivatives thereof may be present in a composition of the present invention in a ratio of about 1:1.

Example compositions of the present invention include, but are not limited to, those provided in Table 1.

TABLE 1

Example compositions of the present invention.

| Ingredient (INCI Name) | Trade Name | Function | % w/w |
|---|---|---|---|
| Purified Water | Purified Water | Diluent | 70%-balance (e.g., 70%-90%) |
| tert-Butyl alcohol (and) denatonium benzoate | SDA 40 B, 190 proof | Solvent | 1%-15% |
| Ethoxydiglycol | Transcutol P | Penetration Enhancer | 1%-10% |
| Tetrapeptide-30 (and) Glycerin | TEGO Pep 4-Even | Skin Brightening | 0.1%-5% |
| Salicylic Acid | Salicylic Acid | Active Ingredient | 0.1%-5% |
| Water (and) Dextran (and) Tripeptide-1 | Kollaren PS 100 | Skin Renewal | 0.1%-5% |
| Polyacrylate Crosspolymer-6 | Sepimax Zen | Thickener | 0.1%-5% |
| Phenoxyethanol (and) Ethylhexylglycerin | Euxyl PE 9010 | Preservative | 0.1%-5% |
| Butylene Glycol (and) Pentylene Glycol (and) Hydroxyphenyl Propamidobenzoic Acid | SymCalmin | Anti-Irritant | 0.01%-2% |
| Sodium Hydroxide | Sodium Hydroxide, NF | pH Adjustment | 0.01%-2% |
| Bisabolol (and) Zingiber Officinale (Ginger) Root Extract | SymRelief 100 | Anti-Irritant | 0.01%-2% |
| Disodium EDTA | Versene NA | Chelating Agent | 0.01%-2% |
| To Make Total | | | 100.0% |

A composition of the present invention may have a pH in a range of about 4 to about 8. In some embodiments, the composition may have a pH of about 4, 4.5, 5, 5.5, 6, 6.5, 7, 7.5, or 8.

A composition of the present invention may have a viscosity in a range of about 5,000 cP to about 25,000 cP, such as, but not limited to, about 5,000 cP to about 20,000 cP or about 7,000 cP to about 15,000 cP. In some embodiments, a composition of the present invention may have a viscosity of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 cP.

In some embodiments, a kit is provided. The kit may comprise a composition of the present invention and optionally one or more (e.g., 1, 2, 3, or more) different compositions. In some embodiments, a kit of the present invention comprising two or more (e.g., 2, 3, 4, 5, 6, 7, or more) separately stored compositions of the present invention. For example, each of the two or more separately stored composition may be in individual containers such as, e.g., vials, pouches, sachets, and/or the like. A kit of the present invention may provide a 7, 14, 21, or 30 day supply of the composition of the present invention.

In some embodiments, a kit of the present invention may separately store one or more (e.g., 1, 2, 3, 4, 5, or more) components of a composition of the present invention (e.g., an API) from one or more (e.g., 1, 2, 3, 4, 5, or more) of the same or different components of the composition. Thus, upon contact, mixing, and/or the like of the separately stored components, the composition is formed, such as, but not limited to, prior to and/or upon application to a subject.

According to some embodiments, a method of the present invention may comprise administering a composition of the present invention to the skin of a subject. In some embodiments, the composition may be topically administered.

In some embodiments, a method of the present invention comprises delivering a therapeutically effective amount of a composition of the present invention to the skin of a subject. As used herein, the term "therapeutically effective amount" refers to an amount of a composition of the present invention that elicits a therapeutically useful response in a subject. Those skilled in the art will appreciate that the therapeutic effects need not be complete or curative, as long as some benefit is provided to the subject. In some embodiments, a therapeutically effective amount of a composition of the present invention may include delivering a therapeutically effective amount of a component of the composition, such as, but not limited to, an active pharmaceutical ingredient.

The present invention finds use in both veterinary and medical applications. Subjects suitable to be treated with a method embodiment of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates (e.g., simians and humans), non-human primates (e.g., monkeys, baboons, chimpanzees, gorillas), and the like, and mammals in utero. Any mammalian subject in need of being treated according to the present invention is suitable. Human subjects of both genders and at any stage of development (i.e., neonate, infant, juvenile, adolescent, adult) may be treated according to the present invention. In some embodiments of the present invention, the subject is a mammal and in certain embodiments the subject is a human. Human subjects include both males and females of all ages including fetal, neonatal, infant, juvenile, adolescent, adult, and geriatric subjects as well as pregnant subjects. In particular embodiments of the present invention, the subject is a human adolescent and/or adult.

Illustrative avians according to the present invention include chickens, ducks, turkeys, geese, quail, pheasant, ratites (e.g., ostrich) and domesticated birds (e.g., parrots and *canaries*), and birds in ovo.

The methods of the present invention may also be carried out on animal subjects, particularly mammalian subjects such as mice, rats, dogs, cats, livestock and horses for veterinary purposes and/or for drug screening and drug development purposes.

In some embodiments of the present invention, the subject is "in need of" a method of the present invention, e.g., the subject has been diagnosed with, is at risk for, and/or is believed to have a disease or disorder that may be treated using a method of the present invention. In some embodiments, the subject has a skin disorder, such as, but not limited to, acne, androgenetic alopecia, atopic dermatitis, seborrheic dermatitis, tinea infections, *Candida* infections, bacterial infections, verruca vulgaris, and/or psoriasis. In some embodiments of the present invention, the subject has an inflammatory skin condition or disorder and/or infection (e.g., impetigo, leishmaniasis, etc.). In some embodiments, a composition of the present invention may be used to treat acne vulgaris. According to some embodiments, a composition and/or method of the present invention may reduce *P. acnes* counts, inflammatory lesions, and/or noninflammatory lesions in a subject.

"Treat," "treating" or "treatment of" (and grammatical variations thereof) as used herein refer to any type of treatment that imparts a benefit to a subject and may mean that the severity of the subject's condition is reduced, at least partially improved or ameliorated and/or that some alleviation, mitigation or decrease in at least one clinical symptom is achieved and/or there is a delay in the progression of the disease, disorder, and/or condition. In particular embodiments, the severity of a skin disorder (e.g., acne) may be reduced in a subject compared to the severity of the skin disorder in the absence of a method of the present invention. In other embodiments, a method of the present invention may prevent and/or treat against infection.

A composition of the present invention may be applied topically to any portion of a subject's skin. However, in some embodiments, the subject's face is treated by a method described herein. Furthermore, in some embodiments, the subject's trunk is treated by a method described herein. In some embodiments, the subject's back, arm(s), hand(s), finger(s), foot, feet, toe(s), and/or genital(s) are treated by a method described herein.

According to some embodiments of the present invention, a method of treating acne vulgaris may be provided, the method comprising topically applying a composition of the present invention to the skin of a subject. A therapeutically effective amount of the composition may be applied.

According to further embodiments of the present invention, a method of reducing inflammatory and/or noninflammatory lesions in a subject may be provided comprising topically applying a composition of the present invention to the skin of the subject. A therapeutically effective amount of the composition may be applied. In some embodiments, the method may reduce inflammatory and/or noninflammatory lesions by about 10% or greater, such as, but not limited to, about 15%, 20%, 25%, 30%, 35%, 40%, 45%, 50%, 55%, 60%, 65%, 70%, 75%, 80%, 85%, 90%, 95%, or more, over a defined period of time compared to a subject who did not apply a composition of the present invention over the same time period. In some embodiments, the subject may see a reduction in inflammatory and/or noninflammatory lesions within about 1, 2, 3, 4, 5, 6, 7, 8, 9, 10, 11, 12, 13, or more week(s). In some embodiments, the method may reduce inflammatory and/or noninflammatory lesions in the skin of the subject within 12 weeks or less, in some embodiments, within 8 weeks or less, and in further embodiments, within 4 weeks or less.

In some embodiments, a method of the present invention may reduce *P. acnes* counts in the subject. In some embodiments, a method of the present invention may reduce *P. acnes* counts by about 10% or greater, such as, but not limited to, about 15%, 20%, 25%, 30%, 35%, 40%, 45%, 50%, 55%, 60%, 65%, 70%, 75%, 80%, 85%, 90%, 95%, or more over a defined period of time compared to a subject who did not apply a composition of the present invention over the same time period. In some embodiments, a reduction in *P. acnes* counts may occur within about 1, 2, 3, 4, 5, 6, 7, 8, 9, 10, 11, 12, 13, or more week(s). In some embodiments, a method of the present invention may reduce *P. acnes* counts in the skin of the subject within 12 weeks or less, in some embodiments, within 8 weeks or less, and in further embodiments, within 4 weeks or less.

A composition of the present invention may have improved tolerability and/or low irritation to the skin of a subject to which it is applied, optionally compared to a current commercial treatment and/or composition (e.g., an over-the-counter composition comprising salicylic acid). In some embodiments, a composition of the present invention has no, low, and/or decreased burning/stinging, redness, dryness, scaling/peeling, and/or pruritis of the skin to which it is applied, optionally compared to a current commercial treatment and/or composition (e.g., an over-the-counter composition comprising salicylic acid).

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A topical composition comprising:
   a diluent, wherein the diluent is water and water is present in an amount of about 60% to about 95% by weight of the topical composition:
   a solvent, wherein the solvent comprises an alcohol:
   a penetration enhancing agent, wherein the penetration enhancing agent comprises a glycol ether;
   a skin brightening agent, wherein the skin brightening agent comprises a peptide comprising the amino acid sequence of SEQ ID NO:1:
   a skin renewal agent, wherein the skin renewal agent comprises a peptide;
   a thickening agent, wherein the thickening agent comprises a polyacrylate polymer;
   an anti-irritant;
   a chelating agent;
   an active pharmaceutical ingredient (API) selected from the group consisting of salicylic acid, a nitric oxide (NO)-releasing compound, and any combination thereof;
   optionally a pH adjustment agent; and
   optionally a preservative.

2. The topical composition of claim 1, further comprising L-arginine, esters thereof, or derivatives thereof; L-citrulline, esters therefor or derivatives thereof; or any combination thereof.

3. The topical composition of claim 1, wherein the water is present in an amount of about 70% to about 90% by weight of the topical composition.

4. The topical composition of claim 1, wherein the alcohol is tert-butyl alcohol.

5. The topical composition of claim 1, wherein the solvent is present in an amount of about 1% to about 20% by weight of the topical composition.

6. The topical composition of claim 1, wherein the glycol ether is ethoxydiglycol.

7. The topical composition of claim 1, wherein the penetration enhancing agent is present in an amount of about 1% to about 10% by weight of the topical composition.

8. The topical composition of claim 1, wherein the skin brightening agent is present in an amount of about 0.1% to about 10% by weight of the topical composition.

9. The topical composition of claim 1, wherein the skin renewal agent is present in an amount of about 0.1% to about 10% by weight of the topical composition.

10. The topical composition of claim 1, wherein the thickening agent is present in an amount of about 0.1% to about 5% by weight of the topical composition.

11. The topical composition of claim 1, wherein the anti-irritant is present in an amount of about 0.1% to about 10% by weight of the topical composition.

12. The topical composition of claim 1, wherein the chelating agent is present in an amount of about 0.01% to about 2% by weight of the topical composition.

13. The topical composition of claim 1, wherein the API is salicylic acid.

14. The topical composition of claim 1, wherein the API is present in an amount of about 0.1% to about 10% by weight of the topical composition.

15. The topical composition of claim 1, wherein the topical composition comprises the pH adjustment agent and the pH adjustment agent is present in an amount of about 0.01% to about 3% by weight of the topical composition.

16. The topical composition of claim 1, wherein the topical composition comprises the preservative and the preservative is present in an amount of about 0.01% to about 3% by weight of the topical composition.

17. The topical composition of claim 1, wherein the API is a NO-releasing compound.

18. A kit comprising the topical composition of claim 1.

19. The kit of claim 18, wherein a first container comprises one or more components of the topical composition and a second container comprises one or more of the same or different components of the topical composition, wherein the first container and second container comprise at least one component that is different or not present in the other container.

\* \* \* \* \*

UNITED STATES PATENT AND TRADEMARK OFFICE
CERTIFICATE OF CORRECTION

PATENT NO. : 11,534,382 B2
APPLICATION NO. : 16/623831
DATED : December 27, 2022
INVENTOR(S) : Stasko et al.

It is certified that error appears in the above-identified patent and that said Letters Patent is hereby corrected as shown below:

On the Title Page

(56) References Cited; U.S. PATENT DOCUMENTS; OTHER PUBLICATIONS; Column 2, Line 38: Please correct "Dimethlcone" to read --Dimethicone--

(56) References Cited; U.S. PATENT DOCUMENTS; OTHER PUBLICATIONS; Page 2, Column 2, Lines 7-8: Please correct the website to read
--https://en.wikipedia.org/w/index.php?title=Polysorbate_20&oldid=758125799--

In the Specification

Column 3, Line 61: Please correct "11%1, 2%1, 3%1, 4%1, 5%1, 6%1, 7%," to read --11%, 12%, 13%, 14%, 15%, 16%, 17%,--

Column 4, Line 2: Please correct "10%1" to read --10%--

Column 4, Line 8: Please correct "Gattefosse" to read --Gattefossé--

Column 5, Line 9: Please correct "5%5.5%," to read --5%, 5.5%,--

Column 11, Line 21: Please correct "10%" to read --1%--

Signed and Sealed this
Ninth Day of May, 2023

*Katherine Kelly Vidal*
Katherine Kelly Vidal
*Director of the United States Patent and Trademark Office*